United States Patent [19]

Lynch

[11] Patent Number: 5,272,080
[45] Date of Patent: Dec. 21, 1993

[54] PRODUCTION OF BUTYRYLCHOLINESTERASE

[75] Inventor: Thomas J. Lynch, Rockville, Md.

[73] Assignee: Pharmavene, Inc., Gaithersburg, Md.

[21] Appl. No.: 657,089

[22] Filed: Feb. 19, 1991

[51] Int. Cl.$^5$ .................. C12N 9/18; A61K 37/48; A61K 37/54
[52] U.S. Cl. .................. 435/197; 435/814; 435/815; 424/94.1; 424/94.6; 210/660
[58] Field of Search .................. 435/197, 814, 815; 424/94.1, 94.6; 210/660

[56] References Cited

U.S. PATENT DOCUMENTS 4,472,320  9/1984  Ashani et al. .................. 260/937
4,963,345  10/1990  Forrest .................. 424/10

OTHER PUBLICATIONS

Connell et al. *Can J. Biochemical Physiology*, 39:1019, 1961.
Lockridge et al. *J. Biol. Chem.* 253:361, 1978.
Schuh, *Anaesthesist* vol. 24, pp. 103–106, 1975.
Ikarashi et al. *J. of Chromotography*. 533 pp. 22–33 1990.

*Primary Examiner*—David M. Naff
*Assistant Examiner*—L. Blaine Lankford
*Attorney, Agent, or Firm*—Susan A. Capello; John G. Gilfillan, III

[57] ABSTRACT

Butyrylcholinesterase is produced in a purity of at least 90% by subjecting plasma fraction IV-4 alone or in admixture with fraction IV-1 to both anion exchange chromatography and affinity chromatography.

7 Claims, 2 Drawing Sheets

FIG. 1

PURIFICATION OF HUMAN BUTYRYLCHOLINESTERASE

| | FRACTION | PROTEIN (mg) | BUTYRYLCHOLINESTERASE | | | |
|---|---|---|---|---|---|---|
| | | | TOTAL (UNITS) | TOTAL (mg) | SPECIFIC ACTIVITY (UNITS/mg) | SPECIFIC ACTIVITY (mg/mg) | YIELD (%) |
| 0. | PLASMA | 5,915,000 | 80,800 | 404 | 0.014 | 0.00007 | — |
| 1. | FRACTION IV-4 | 584,000 | 79,950 | 400 | 0.137 | 0.0007 | 100 |
| 2. | EXTRACT | 435,000 | 69,630 | 348 | 0.160 | 0.0008 | 87 |
| 3. | DE-I POOL | 31,713 | 53,460 | 267 | 1.69 | 0.0084 | 67 |
| 4. | PAM-I POOL | 1,727 | 38,670 | 193 | 22.40 | 0.112 | 48 |
| 5. | DE-II POOL | 277 | 31,864 | 159 | 115.00 | 0.575 | 40 |
| 6. | PAM-II POOL | 169 | 31,380 | 157 | 181.00 | 0.905 | 39 |

RESULTS OF PURIFICATION USED AS EXAMPLE IN TEXT. THE PROCESS BEGAN WITH 1,825 OF FRACTION IV-4 WHICH IS THE AMOUNT OF MATERIAL PRECIPITATED FROM APPROXIMATELY 91 LITERS OF HUMAN PLASMA. THE VALUES FOR PLASMA ARE ESTIMATES BASED ON THIS VOLUME, A MEAN PROTEIN CONCENTRATION OF 65 mg/ml AND A MEAN BUTYRYLCHOLINESTERASE CONCENTRATION OF 0.9 UNITS/ml (4.4 mg/LITER).

FIG. 2

SUMMARY OF BUTYRYLCHOLINESTERASE PREPARATIONS

| PREPARATION | YEILD (mg) | YEILD (%) | BUTYRYLCHOLINESTERASE SPECIFIC ACTIVITY (U/mg) | BUTYRYLCHOLINESTERASE SPECIFIC ACTIVITY (mg/mg) |
|---|---|---|---|---|
| 1 | 157 | 39 | 181 | 0.91 |
| 2 | 157 | 43 | 195 | 0.97 |
| 3 | 123 | 35 | 191 | 0.95 |

PRODUCTION OF BUTYRYLCHOLINESTERASE

The present invention relates to butyrylcholinesterase and more particularly to the production and use thereof.

BACKGROUND OF THE INVENTION

Butyrylcholinesterase (acylcholine acylhydrolase, EC 3.1.1.8, also known as pseudocholinesterase) is an enzyme found in the plasma, among other tissues, of all vertebrates in which it has been sought (Silver, A. *The Biology of Cholinesterase*, North-Holland, Amsterdam, 1974). The existence of this enzyme in human plasma was formally demonstrated 50 years ago (Alles, G. A. and Hawes, R. C., *J. Biol. Chem.*, 133:375, 1940), but its normal physiological role remains unknown. However, butyrylcholinesterase is responsible for the hydrolysis and inactivation of muscle relaxants such as succinylcholine and related anaesthetics (LaDu, B. M., *Ann. N.Y. Acad. Sci.*, 179:648, 1971), substances currently in clinical use. Butyrylcholinesterase is also responsible for degrading the majority of the cocaine ingested by a drug abuser (Stewart, D. J. et al., *Life Scie.*, 20:1557, 1977; Jatlow, P., et al., *Anesth. Anag.*, 58:235, 1979; Stewart, D. J. et al., *Clin. Pharmacol. Ther.* 25:464, 1979).

The gene for human butyrylcholinesterase exists as a "wild-type" (normal) allele and several defective alleles which are present in as much as 5% of the population (reviewed in Whittaker, M., *Anaesthesia*, 35:174, 1980; Evans, R. T., *CRC Crit. Rev. Clin. Lab. Sci.*, 23:35, 1985). In approximately 1 in 2800 individuals, their genotype results in a severe deficiency in butyrylcholinesterase. When these individuals are treated with succinylcholine during the induction of general anaesthesia prior to surgery, the resulting paralysis is greatly prolonged compared to the normal population. During this period the patient is unable to breathe, a condition known as apnea, and must be artificially ventilated until the succinylcholine is degraded by secondary mechanisms. This is considered to be a potentially life-threatening situation. Butyrylcholinesterase activity may also be reduced sufficiently from normal levels to induce succinylcholine sensitivity during pregnancy (Wildsmith, J. A. W., *Anaesthesia*, 27:90, 1972; Weissman, D. B. and Ehrenwerth, J., *Anesth. Analg.*, 62:444, 1983), by certain diseases such as hepatitis (Singh, D. C. et al., *J. Ind. Med. Assoc.*. 66:49, 1976) or as a consequence of various medications (Foldes, F. F., *Enzymes in Anaesthesiology*, Springer-Verlag, N.Y., 1978).

Toxicologically, cocaine is also well tolerated by the majority of the population. Nevertheless there is a small incidence of sudden death related to acute cocaine abuse see Clouet, D. et al., *Mechanisms of Cocaine Abuse and Toxicity*, NIDA Research Monograph 88; Johanson, C. and Fischman, M. W., *Pharmacol. Rev.* 41:3, 1889). The physiological basis for this difference in susceptibility is not known. However, it has been argued that a deficiency in butyrylcholinesterase could contribute to an individual's sensitivity (Stewart, D. J. et al, supra, 1979; Jatlow, P., (supra, 1979; Anton, A. H., *Drug Intell. Clin. Pharm.*, 22:914, 1988; Devenyl, P., *Ann. Int. Med.*. 110:167, 1989).

A number of compounds of the organonhosphate type are used as pesticides (e.g. malathion) or neurotoxic chemical warfare agents (e.g. soman; Silver, A., supra, 1974; Aldridge, W. N. and Reiner, E., *Enzyme Inhibitors as Substrates*, North-Holland, Amsterdam, 1972). These compounds exert their toxic effects by inhibiting acetylcholinesterase, an enzyme found on erythrocytes and at cholinergic synapses where it plays an essential role in proper neurological and neuromuscular function. Butyrylcholinesterase is also inhibited by these compounds because of the similarity of its active site to that of acetylcholinesterase (Soreq, H. and Prody, C. A., in: *Computer Assisted Modeling of Receptor-Ligand Interactions*, Alan R. Liss, N.Y., 1989). Therefore, plasma butyrylcholinesterase and erythrocyte acetylcholinesterase afford some protection to synaptic acetylcholinesterase from these neurotoxins since the toxins themselves are inactivated by the reactions that inhibit these enzymes. Only those toxin molecules that survive in the circulatory system without reacting with the plasma cholinesterases are capable of attacking synaptic acetylcholinesterase. It follows that an individual's susceptibility to these compounds is determined in part by the amount of cholinesterase present in the blood. It has been shown that administration of bovine serum acetylcholinesterase to mice increases their resistance to organophosphate poisoning (Rauch, L., Ashani, Y., Levy, D., de la Hoz, D., Wolfe, A. D. and Doctor, B. P., *Biochem. Pharmacol.*, 38:529, 1989).

Butyrylcholinesterase is present in human plasma, serum or whole blood. Methods have been developed for obtaining butyrylcholinesterase from plasma. These can be classified in two groups: those in which the plasma is first fractionated by a precipitation method and those in which the plasma is chromatographed directly.

The earliest methods employed ethanol or ammonium sulfate as precipitants. Cohn et al. (*J. Amer. Chem. Soc.*, 68:459, 1946) found that the majority of "plasma esterase" partitioned into one fraction, designated IV-4, during the fractionation of human plasma by ethanol. Subsequently, Surgenor and Ellis (*J. Amer. Chem. Soc.*, 76:6049, 1954) extended this method by repetitive precipitations to produce human butyrylcholinesterase (designated fraction IV-6-4) of about 20% purity with a yield of 7%. An intermediate fraction (IV-6-3) obtained by this procedure was further purified by chromatography on hydroxylapatite and Dowex anion exchange resin (Malstrom et al., *Acta Chem. Scand.*, 10:1077, 1956). While this last procedure produced butyrylcholinesterase of high (at least 80%) purity, the overall recovery was poor, no better than 3%.

Several other methods have been developed which employ ammonium sulfate precipitation as an early step. These procedures either produced crude enzyme (no more than 10% purity; Goedde, H. W. et al., *Human Genet.*, 1:311, 1965) or incorporated preparative electrophoresis, a technique which is impractical for any large scale process, to achieve higher degrees of purity with about 10% yields (Svensmark, O. and Kristensen, P., *Biochim. Biophys. Acta.* 67:441, 1963; Haupt, H. et al., *Blut*, 14:65, 1966). Because of these drawbacks, these methods have been abandoned for any application requiring highly purified butyrylcholinesterase in large (commercial) quantities.

Present methods employ the chromatographic purification of butyrylcholinesterase from defibrinated plasma and are based on the ability of the enzyme to bind to conventional anion exchange resins under acidic (pH 4) conditions (Connell, G. E. and Shaw, R. W., *Can. J. Biochem. Physiol.*, 39:1019, 1961). When optimized, anion exchange chromatography at pH 4 of human plasma achieves a 400- to 800-fold purification of butyrylcholinesterase (i.e. to a purity of 2-4%) in a single step (Das, P. K. and Liddell, J., *Biochem. J.*, 116:875, 1970; Meunsch, H. et al., *Eur. J. Biochem.*, 70:217, 1976). The subsequent steps used by these groups to further purify the enzyme were supplanted by affinity chromatography on procainamide-agarose (Lockridge, O. and LaDu, B. N., *J. Biol. Chem.*, 253:361, 1978) which achieved a two-step purification of butyrylcholinesterase to 88% purity with a 70% yield. Further refinements of the method added an additional anion exchange step at pH 7 (Lockridge, O. and LaDu, B. N., *J. Biol. Chem.*, 287:12012, 1982; Lockridge, O. et al., *J. Biol. Chem.*, 262:549, 1987), producing a virtually homogeneous enzyme with an overall yield of 30-40%.

SUMMARY OF THE INVENTION

In accordance with an aspect of the present invention, butyrylcholinesterase is recovered from the plasma fraction known as IV-4 or from a mixed plasma fraction of fractions IV-4 and IV-1 by use of a combination of anion exchange chromatography and affinity chromatography. In accordance with a preferred aspect, the procedure involves an initial anion exchange chromatography, followed by affinity chromatography, with the above two steps repeated at least one more time.

BRIEF DESCRIPTION OF THE DRAWINGS

FIG. 1 shows the quantative analyses of each step of the preparation in the purification of human butyrylcholinesterase.

FIG. 2 shows a comparison of the results of the purification illustrated in the example of preparation 1 with two other butyrylcholinesterase preparations.

DETAILED DESCRIPTION OF THE INVENTION

The recovery of butyrylcholinesterase from the noted fractions by use of a combination of anion exchange chromatography and affinity chromatography can produce butyrylcholinesterase in a purity of at least 80%, (preferably at least 90%) and in yields of at least 30% based on the average amount of butyrylcholinesterase present in human plasma.

The anion exchange column may be any one of a wide variety of anion exchange columns. As representative materials which are effective for recovery of butyrylcholinesterase from the noted fractions there may be mentioned media comprising amines, tertiary amines or quaternary amines covalently bound to a supporting medium such as dextran, agarose, polyacrylamide, polystyrene, silica or acrylic or vinyl polymers. A preferred column is a crosslinked diethylaminoethyl-agarose column (for example a DEAE-Sepharose Fast Flow medium sold by Pharmacia). In a preferred embodiment, such anion exchange chromatography is effected at a pH of from 4.0 to 4.5.

The affinity chromatography may be accomplished by any of a variety of materials suitable for recovering butyrylcholinesterase by affinity chromatography. As representative examples of such materials there may be mentioned any substrate or reversible inhibitor of butyrylcholinesterase, an antibody specific for butyrylcholinesterase or a lectin particularly any of those capable of binding sialic acid residues with high affinity, any or all of which could be covalently bound, directly or through a "spacer", to a supporting medium suitable for chromatography such as those mentioned above. A preferred material is procainamide (p-amino-N-(2-diethylaminoethyl)benzamide) covalently coupled to aminohexanoic acid-agarose. In accordance with a preferred embodiment, the affinity chromatography is run within the range of pH (6-9) in which the butyrylcholinesterase activity is optimal.

The hereinabove noted human plasma fractions are commercially available and may be produced by known procedures. In particular as known in the art such fractions are obtained from plasma by use of ethanol precipitation.

Butyrylcholinesterase, whether in plasma or in a highly purified form, is not sufficiently stable at elevated temperatures to permit heat-inactivation of any residual viruses in a preparation of this enzyme. However, we have determined that the enzyme is unaffected by extended treatment with tri-n-butyl phosphate and sodium cholate, in concentrations sufficient to inactivate viruses such as hepatitis B virus, non-A, non-B hepatitis virus and HTLV-III (Horowitz, B, Wiebe, M. E., Lippin, A. and Stryker, N. H., *Transfusion*, 25, 516, 1985; Edwards, C. A., Piet, MPJ, Chin, S. and Horowitz, B., *Vox Sanquinis*, 52:53, 1987). Since the solvent and detergents used in this procedure are readily removed by the chromatographic methods used to purify butyrylcholinesterase, the viral inactivation may be performed at any stage of the purification. Therefore, by including this procedure in the purification process and by passing the purified enzyme through a filter with an effective pore size not larger than 0.22 microns, a sterile and virally-inactive preparation of fully active butyrylcholinesterase may be obtained.

The invention will be further described with respect to the following examples; however, the scope of the invention is not limited thereby. Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned hereunder are incorporated herein by reference.

MATERIALS AND METHODS

Enzyme Assays

Butyrylcholinesterase is assayed by monitoring the decrease in optical density at 240 nm during the hydrolysis of 50 $\mu$M benzoylcholine at 25° C. in M/15 phosphate buffer at pH 7.4 (Kalow, W. and Lindsay, A., *Can. J. Biochem.*, 33:868, 1988). The concentration of enzyme is adjusted so that the rate of hydrolysis is constant for at least one minute. Hydrolysis rates are calculated from the difference in extinction coefficients between products and substrate of 6700 $M^{-1} cm^{-1}$. One unit of activity is that amount of enzyme required to hydrolyze 1 $\mu$mol of substrate per minute. Under these conditions 1 mg of butyrylcholinesterase is equivalent to 200 units of enzyme activity, alternatively expressed a specific activity of 200 units/mg (Lockridge and LaDu, supra, 1982). Other substrates or assay methods could also be used.

Electrophoresis

Separations in the presence of SDS are performed according to Laemmli (*Nature*, 227:680, 1970). Nondenaturing gels are run according to Juul (*Clin. Chem. Acta.*, 19:208, 1968) and stained for esterase activity using α-naphthyl butyrate as a non-specific substrate able to detect contaminating esterases if present as well as butyrylcholinesterase (Harris, H. et al., *Nature*, 196:12296, 1862).

Chromatography Medium

For anion exchange chromatography, a mechanically and chemically stable medium, such as DEAE-Sepharose Fast Flow (Pharmacia), is preferred to facilitate cleaning and regeneration. Other anion exchange media, could also be used.

For affinity chromatography, procainamide (p-amino-N-(2-diethylaminoethyl)benzamide) is covalently coupled to 6-aminohexanoic acid-agarose via a condensation reaction mediated by 1-ethyl-3-(3-dimethylaminopropyl) carbodiimide (EDC). The reaction is run in $H_2O$ in a volume about 5 times that of the swollen agarose which contains at least 15 μmol of carboxyl groups per ml of swollen gel. To this is added a 4-fold molar excess (with respect to the immobilized carboxyl groups) of procainamide and a 40-fold molar excess of EDC. The mixture is stirred for 24 hours; during the first 4 hours the pH is maintained at about 5.28 by the addition of 0.1 M HCl. The gel is washed free of unreacted material and urea and packed into an appropriate column. The derivatization is nearly quantitative under these conditions, at least 15 μmol of procainamide are coupled to each ml of agarose.

Protein Concentration

The concentration of protein during the purification is monitored by a colorimetric method (Bradford, M. M., *Anal. Biochem.*, 72:248, 1976) or by optical absorbance at 280 nm. The concentration of purified butyrylcholinesterase is determined by its absorbance at 280 nm assuming an extinction coefficient of 1.8 ml.mg$^{-1}$cm$^{-1}$ (Lockridge et al., supra, 1979).

Purification Process

The starting material is human plasma pooled from multiple individuals. The plasma may be used as is, either fresh or "outdated", or after conventional treatments to produce "cryo-poor" or defibrinated plasma. The plasma is then treated by a series of ethanol additions and pH adjustments as described (Cohn, E. J. et al., supra, 1946) or by any modification of this method designed to effect an equivalent fractionation of the plasma. The precipitate designated Fraction IV-4 or the combined precipitates designated Fraction IV-1 plus IV-4 are collected. This material may be immediately processed further or stored frozen for later use.

The butyrylcholinesterase and other components of the ethanol precipitate are resolubilized in 4-5 volumes (relative to the weight of the protein precipitate) of buffer (20 mM acetate, citrate or the like) or of deionized water, titrated to pH 4 with the acidic component of the buffer, clarified by centrifugation or filtration and dialyzed to near equilibrium against 25 volumes of the same buffer, the order of the latter three steps being unimportant. In this and all subsequent steps in which the composition of the butyrylcholinesterase solution must be adjusted, the methods of dialysis, gel filtration or dilution may be used.

The butyrylcholinesterase solution is then applied to an anion exchange column (no larger than ⅛ the volume of the applied solution) equilibrated with the same buffer as used for dialysis. The column is washed with this buffer to remove the majority of unbound material and the butyrylcholinesterase is eluted by increasing the ionic strength of the buffer flowing through the column. That part of the eluate containing butyrylcholinesterase is titrated to pH 7 and diluted with an approximately equal volume of water. This solution is then applied to a procainamide-agarose column equilibrated with a moderate ionic strength buffer at pH 7.0-7.4 (such as 100 mM NaCl, 20 mM phosphate). The volume of this column is about 1/10 the volume of the original protein precipitate. The column is washed with about 2 volumes of equilibration buffer and the butyrycholinesterase is eluted with a gradient of increasing ionic strength, to the equivalent of 1 M NaCl, in a total of 7-10 column volumes. That part of the eluate containing butyrylcholinesterase is dialyzed to near equilibrium against 15-20 volumes of a low ionic strength buffer, such as 20 mM phosphate, at pH 7.4. This solution is applied to a second anion exchange column equilibrated with the same buffer used for dialysis. The volume of this column is about one tenth that of the first anion exchange column. The butyrylcholinesterase is eluted with a gradient of increasing ionic strength to the equivalent of 250 mM NaCl in a total of 4 column volumes. That part of the eluate containing butyrylcholinesterase is diluted with one volume of a low ionic strength buffer, such as 20 mM phosphate at pH 7.4. This solution is applied to a second procainamide-agarose column of about one tenth the volume of the first. This column is washed and eluted as for the first except that all volumes are adjusted to maintain the same proportions relative to the size of the column. The butyrylcholinesterase eluting from this column is sufficiently free of other plasma proteins by the criteria of electrophoretic homogeneity and enzyme activity.

EXAMPLE

Purification of Butyrylcholinesterase From Human Plasma Fraction IV-4

The quantitative analyses of each step in this preparation is found in Table 1. The starting material was Fraction IV-4 (Lot No. 0208, obtained from American Red Cross recovered human plasma and processed by Baxter, Hyland Division). This material was frozen as a protein precipitate and stored at −70° C. until used. Twelve hours prior to extraction, the precipitate was transferred to −20° C. All subsequent steps were performed at 4°-6° C.

1825 grams of Fraction IV-4 was extracted with 9.1 liters of 20 mM sodium acetate buffer, pH 4.0, by mechanical stirring for 18 hours. The resulting suspension was centrifuged for 90 minutes at 13,700 x g and the combined supernatants were dialyzed overnight against 45 liters of the same buffer. The following morning the sample was transferred to a fresh 45-liter batch of dialysis buffer for an additional 24 hours. Following dialysis, the pH required no further adjustment but a flocculence had developed which was removed by centrifugation as before. The final volume of this solution (EXTRACT) was 10.9 liters.

The extract was loaded on a column packed with 5 liters of DEAE-Sepharose Fast Flow previously equilibrated with the same buffer used for extraction and dialysis. The column was washed with 10 liters of this buffer and then eluted with 5 liters of 200 mM NaCl in the same buffer. Those fractions containing butyrylcholinesterase were pooled in a final volume of 3.3 l (DE-I pool).

The DE-I pool was titrated with 380 ml of 0.8 M sodium phosphate dibasic to pH 7.0 and diluted with 4 liters of water. This solution was then loaded on a column packed with 200 ml of procainamide-agarose previously equilibrated with 20 mM phosphate buffer, pH 7.4, 100 mM NaCl, 1 mM EDTA. The column was washed with 400 ml of the same buffer and with 600 ml of the same buffer but with 200 mM NaCl. The column was then eluted with a 1.4-liter linear gradient to 1 M NaCl. Those fractions containing butyrylcholinesterase were pooled in a final volume of 1 liter (PAM-I pool).

The PAM-I pool was dialyzed overnight against 18 liters of 20 mM phosphate buffer, pH 7.4, and loaded on a column packed with 480 ml of DEAE-Sepharose Fast Flow previously equilibrated with the same buffer. The column was immediately eluted with a 2-liter gradient from 80 to 250 mM NaCl in the same buffer. Those fractions containing butyrylcholinesterase were pooled in a final volume of 270 ml (DE-II pool).

The DE-II pool was dialyzed overnight against 2 liters of 20 mM phosphate buffer, pH 7.4, 100 mM NaCl, 1 mM EDTA, and loaded on a column packed with 20 ml of procainamide-Sepharose equilibrated with the same buffer. The column was washed with 120 ml of 200 mM NaCl in the same buffer and eluted with a 280 ml gradient to 1 M NaCl. Those fractions containing butyrylcholinesterase were pooled in a final volume of 200 ml (PAM-II pool).

The PAM-II pool was concentrated to a final volume of 26 ml in a pressure filtration device fitted with a 50,000 nominal molecular weight cut-off filter. The solution was then dialyzed overnight against 2 liters of 20 mM phosphate buffer, pH 7.4, 184 mM NaCl, 0.8 mM EDTA. The purified butyrylcholinesterase was stored at 4° C.

Characterization of Purified Butyrylcholinesterase

The principal criterion for evaluating the purified enzyme is its catalytic activity. When measured using benzoylcholine as the substrate, the specific activity of the preparation described here was 181 Units/mg (Table 1). This activity is 91% of the maximum reported for the homogeneous enzyme and indicates the presence of no more than 9% contaminating proteins and no more than 9% inactivation of the butyrylcholinesterase during its purification. Using a second substrate, propionylthiocholine, the specific activity of this preparation was 700 Units/mg, equal to the previously repdrted maximum (Lockridge and LaDu, supra, 1982).

The product of this preparation was also analyzed on SDS gels. By this method, purified butyrylcholinesterase is composed of a major polypeptide of $M_R$ 90,000, corresponding to the monomeric subunit, and a minor band of $M_R$ 180,000. It has previously been shown that purified human butyrylcholinesterase includes a $M_R$ 180,000 dimer (presumably crosslinked by covalent bonds other than disulfides) of the predominant monomeric subunit (Lockridge et al., supra. 1979). Therefore both high and low molecular weight bands on the SDS gel comprise butyrylcholinesterase. A number of minor contaminating polypeptides account for a small fraction of the protein present, consistent with the high purity of the enzyme estimated from its specific activity.

During electrophoresis under non-denaturing conditions, the native butyrylcholinesterase migrates as a single band with a $M_R$ 340,000. This agrees with the mass of the tetrameric enzyme measured by hydrodynamic methods (Haupt, H., et al., supra. 1966). Furthermore, histochemical staining of this type of gel for esterase activity demonstrates that the enzyme activity is in fact associated with this protein and that no other esterases are detectable (not shown).

The purification method itself appears to be reproduceable. Table II compares the results of the purification illustrated here (preparation 1) with two others. The yields range from 35% to 43% and the purities from 91% to virtual homogeneity. The compositional features of all three preparations, both on non-denaturing and SDS gels, are similar.

The buffer selected for the storage of the purified butyrylcholinesterase is an isotonic phosphate buffered saline, a suitable vehicle for injection. The enzyme is remarkably stable when refrigerated at high concentrations (3-6 mg/ml) in the buffer. During a 3 month period, less than 8% of the original activity was lost. This indicates that an injectable formulation of this enzyme can be stored for prolonged periods.

The combination of the ethanol-precipitation method to produce Fraction IV-4 with the chromatographic techniques herein described affords at least a 10-fold scale-up of the previously most efficient procedure for purifying butyrylcholinesterase. Specifically, the volumes and amounts of protein involved in a procedure starting with Fraction IV-4 are 10% or less of those with whole plasma as the starting material. Moreover, the size of the first anion exchange column, relative to the amount of enzyme produced, has been reduced 20-fold from the original methods referenced above. These two improvements and the purity, stability and activity of the butyrylcholinesterase isolated by this method make the commercial production of this enzyme feasible.

The butyrylcholinesterase produced in accordance with the present invention has a purity of at least 90% and has a wide variety of potential uses.

One use is to reverse the effects of succinylcholine in patients having a deficiency in butyrylcholinesterase to prevent apnea during general anaesthesia. Thus, in accordance with an aspect of the present invention, a person have a deficiency in butyrylcholinesterase is treated to reverse the effects of succinylcholine by administering butyrylcholinesterase which has a purity of at least 80% (and preferably at least 90%) in an amount effective to reverse the effects of succinylcholine. An effective treatment with butyrylcholinesterase could preceed the administration of succinylcholine in those cases in which a deficiency in butyrylcholinesterase is known or suspected. Alternatively, treatment with butyrylcholinesterase could follow administration of succinylcholine when an abnormal response to the drug is manifested.

In general, the butyrylcholinesterase is administered in an amount of at least 0.01 mg/kg body weight (and preferably at least 0.1 mg/kg body weight). In general, the amount need not exceed 4.0 mg/kg body weight (and preferably need not exceed 0.4 mg/kg body weight.

The butyrylcholinesterase of such purity is employed in combination with a pharmaceutically acceptable carrier. The carrier which is selected is dependent upon the method of administration. Such methods of administration include: intravenous injection, intramuscular injection, inhalation of an aerosol form or as eye drops. The preferred form of administration could be intravenous injection, for which method the aforementioned carrier, phosphate-buffered isotonic saline, would be preferred. For other methods of application, the inclusion of carrier proteins (such as human serum albumin), anti-oxidants, surfactants, anti-foaming agents may be appropriate.

In general, the butyrylcholinesterase of at least 90% purity is present in such pharmaceutical composition in an amount of from 3 mg/ml to 30 mg/ml or more.

The butyrylcholinesterase produced in accordance within the present invention may also be employed to inactivate other pharmaceuticals, such as chloroprocaine, mivacurium, vecuronium, etc., which are substrates for this enzyme, in those individuals with a genetic, induced or acquired deficiency in butyrylcholinesterase. Butyrylcholinesterase may also be administered in order to inactive and thereby reduce the toxic effects of cocaine or of other non-medically and/or illicitly administered compounds that are substrates for this enzyme. The butyrylcholinesterase would be administered in amounts effective to reduce the toxic effect of cocaine, which amounts are similar to those hereinabove noted with respect to the treatment of apnea.

Butyrylcholinesterase may also be administered to increase resistance (in both butyrylcholinesterase-normal and butyrylcholinesterase-deficient individuals) to any of the carbamates and organophosphates used as insecticides or neurotoxins.

For this last application, the enzyme may be administered prior to an anticipated exposure to the toxin, as a prophyllactic, or as a therapeutic administered after an exposure to reduce pools of unreacted toxin in the body. Butyrylcholinesterase could be used in this application alone or in conjunction with a nucleophilic compound (e.g. an oxime). The nucleophilic would hydrolyze the initial adduct between toxin and enzyme before the adduct is converted to an essentially irreversible form. In this way active enzyme would be regenerated from the enzyme-toxin complex. Such a nucleophile could be administered together with, prior to or after the enzyme. The nucleophilic could be administered by the same route as the enzyme or by intramuscular injection.

The dosage of the nucleophilic would be similar to that in current medical practice (approximately 50 mg/kg of body weight) but would be rendered more effective by the presence of higher concentrations of butyrylcholinesterase in the plasma. The butyrylcholinesterase is administered in amounts effective for reducing the toxic effect of a toxin such as a carbamate or organophosphate with such amounts generally being the amounts hereinabove described with respect to the treatment of apnea.

The butyrylcholinesterase produced and used in accordance with the present invention has a purity of at least 90% and a specific activity which is at least 90% of the theoretical maximum specific activity (theoretical maximum is 200 $\mu$mol min$^{-1}$ mg$^{-1}$ or 280 s$^{-1}$ when assayed with 50 $\mu$M benzoylcholine as substrate at 25° C.). The butyrylcholinesterase is preferably used in a high concentration greater than 2 mg/ml in an appropriate pharmaceutical carrier such as an injectable carrier.

Numerous modifications and variations of the present invention are possible in light of the above teachings; therefore, within the scope of the appended claims the invention may be practiced otherwise than as particularly described.

What is claimed is:

1. A process for obtaining butyrylcholinesterase, from plasma comprising:
   subjecting at least a portion of plasma fraction IV-4 or a mixture of plasma fraction IV-4 and plasma fraction IV-1 to both anion chromatography and affinity chromatography to recover therefrom butyrylcholinesterase in a purity of at least 90%.

2. The process of claim 1 wherein the plasma fraction is initially subjected to anion chromatography followed by affinity chromatography.

3. The process of claim 2 wherein the anion chromatography is effected at a pH of from 3.8 to 4.2.

4. The process of claim 3 wherein the affinity chromatography is effected at a pH of from 6.0 to 9.0.

5. The process of claim 4 wherein the anion chromatography is effected on a crosslinked diethylaminoethyl agarose column.

6. The process of claim 5 wherein the affinity chromatography is effected on a column of procainamide covalently coupled to aminohexanoic acid-agarose.

7. The process of claim 6 wherein the combination of anion and affinity chromatography is effected at least twice.

* * * * *